United States Patent
Choi et al.

(10) Patent No.: US 8,449,954 B2
(45) Date of Patent: May 28, 2013

(54) COMPOUND HAVING PHOTOREACTIVE FUNCTIONAL GROUP, PHOTOREACTIVE POLYMER, AND ALIGNMENT FILM COMPRISING THE SAME

(75) Inventors: Dai-Seung Choi, Daejeon (KR); Sung-Ho Chun, Daejeon (KR); Young-Chul Won, Daejeon (KR); Dong-Woo Yoo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 28 days.

(21) Appl. No.: 13/177,399

(22) Filed: Jul. 6, 2011

(65) Prior Publication Data

US 2012/0010381 A1   Jan. 12, 2012

(30) Foreign Application Priority Data

Jul. 7, 2010 (KR) .......... 10-2010-0065570
Mar. 25, 2011 (KR) .......... 10-2011-0027125

(51) Int. Cl.
  *C09K 19/38* (2006.01)
  *C08F 36/20* (2006.01)
  *C08G 61/08* (2006.01)
  *C07C 69/76* (2006.01)
  *C07C 69/753* (2006.01)
  *C07C 49/792* (2006.01)
  *C08F 4/80* (2006.01)

(52) U.S. Cl.
  USPC ............ 428/1.2; 522/183; 526/256; 526/259; 526/265; 526/270; 526/282; 526/309; 560/51; 560/120; 560/128; 568/326; 568/327; 568/329

(58) Field of Classification Search
  USPC .... 526/282, 309, 256, 259, 265, 270; 560/51, 560/120, 128; 568/308, 326, 327, 329; 428/1.2; 522/183
  See application file for complete search history.

(56) References Cited

U.S. PATENT DOCUMENTS

| | | | |
|---|---|---|---|
| 5,464,669 | A | 11/1995 | Kang et al. |
| 6,762,268 | B2 | 7/2004 | Shin et al. |
| 2006/0160970 | A1* | 7/2006 | Kim et al. .............. 526/171 |
| 2010/0047481 | A1 | 2/2010 | Choi et al. |
| 2010/0296032 | A1 | 11/2010 | Shin et al. |
| 2011/0043731 | A1 | 2/2011 | Shin et al. |

FOREIGN PATENT DOCUMENTS

| | | |
|---|---|---|
| CN | 101830961 A | 9/2010 |
| JP | 62-223153 | 10/1987 |
| JP | 11-181127 | 7/1999 |

(Continued)

OTHER PUBLICATIONS

Reznikov et al. "Peculiarity of an Oblique Liquid Crystal Alignment Induced by a Photosensitive Orientant" Jpn, J. Appl. Phys. vol. 34 (1995) pp. L 1000-L 1002, Part 2, No. 8A, Aug. 1, 1995.

(Continued)

*Primary Examiner* — Fred M Teskin
(74) *Attorney, Agent, or Firm* — McKenna Long & Aldridge, LLP

(57) ABSTRACT

The present invention relates to a specific photoreactive polymer that shows excellent alignment stability and thermal stability together with excellent liquid crystal alignment, thereby being desirably used in an alignment film of a liquid crystal display device, a compound having a photoreactive functional group that is used as a monomer for the preparation of the photoreactive polymer, and an alignment film.

15 Claims, 3 Drawing Sheets

FOREIGN PATENT DOCUMENTS

| | | |
|---|---|---|
| JP | 2003-082071 | 3/2003 |
| KR | 2002-0068195 | 8/2002 |
| KR | 10-0451643 | 10/2004 |
| KR | 10-0671753 B1 | 1/2007 |
| KR | 10-2009-0079842 | 7/2009 |
| KR | 10-2009-0079843 | 7/2009 |
| KR | 10-2010-0021751 | 2/2010 |

OTHER PUBLICATIONS

Schadt et al. "Surface-Induced Parallel Alignment of Liquid crystals by Linearly Polymerized Photopolymers", Jpn, J. Appl. Phys. vol. 31 (1992) pp. 2155-2164, Part 1, No. 7, Jul. 1992.

Rehab, Ahmed, "Negative Photoresist Materials Based on Poly(Norbornene Derivatives-co-styrene-co-maleic Anhydride)", Department of Chemistry, Faculty of Science, Tanta University, Tanta, Egypt, Journal of Macromolecular Science, Part A: Pure & Applied Chemistry, vol. 42, pp. 327-339, 2005.

Rehab, Ahmed, "Studies of Photoreactive Poly(Norbornene Derivatives) Bearing Chalcone Units", Department of Chemistry, Faculty of Science, Tanta University, Tanta, Egypt, Journal of Macromolecular Science, Part A, Pure & Applied Chemistry, vol. A40, No. 7, pp. 689-703, 2003.

Enes, Roger F. et al., "Synthesis and antioxidant activity of [60]fullerene-flavonoid conjugates", Department of Chemistry, University of Aveiro, 3810-193 Aveiro, Portugal, Tetrahedron, vol. 65, pp. 253-262, 2009.

Kim et al. "Modification of Poly(vinyl cinnamate) Photo-alignment Layers Using Polymerizable Mesogens", Korean Journal of Chemical engineering, vol. 17, No. 1, p. 17-21, 2000.

Lee et al. "Synthesis of Poly(cinnam-4"-yl methyl methacrylate) Derivatives and their Thermal Stability as Photoalignment Layer", Bull. Korean Chem. Soc 2001, vol. 22, No. 2, p. 179-182.

* cited by examiner

COMPOUND HAVING PHOTOREACTIVE FUNCTIONAL GROUP, PHOTOREACTIVE POLYMER, AND ALIGNMENT FILM COMPRISING THE SAME

This application claims priority to Korean Application Nos. 10-2010-0065570, filed on Jul. 7, 2010, and 10-2011-0027125, filed Mar. 25, 2011, which are both hereby incorporated by reference in their entirety.

BACKGROUND OF THE INVENTION (a) Field of the Invention

The present invention relates to a novel compound having a photoreactive functional group, a photoreactive polymer, and an alignment film comprising the same. More particularly, the present invention relates to a photoreactive polymer that shows excellent alignment stability and thermal stability together with excellent liquid crystal alignment, thereby being desirably used in an alignment film of a liquid crystal display device, a compound having a photoreactive functional group that is used as a monomer for the preparation of the photoreactive polymer, and an alignment film.

(b) Description of the Related Art

In recent years, as a liquid crystal display has become bigger, its application has been expanded from personal mobile phone or notebook computer to wall-mounted television, and thus it is required to ensure the high definition, the high quality, and the wide viewing angle in respects to the liquid crystal display. In particular, since a thin film transistor liquid crystal display (TFT-LCD) driven by a thin film transistor independently drives each of pixels, a response rate of the liquid crystal is very high, and thus a high-quality dynamic image can be realized. Accordingly, the application range thereof is expanded. In order to use liquid crystals as an optical switch in the TFT-LCD, liquid crystals needs to be initially oriented in a predetermined direction on a thin film transistor, which is disposed in the most inner portion of a display cell. For this purpose, a liquid crystal alignment film is used.

To achieve the liquid crystal alignment, a rubbing process is applied, in which a heat resistant polymer such as polyimide is applied on a' transparent glass to form a polymer alignment film and the alignment film is rubbed by rotating a rotation roller wound with a rubbing cloth made of nylon, rayon or the like at a high speed.

However, since the rubbing process may cause mechanical scratches or high static electricity on the surface of the liquid crystal alignment material during the rubbing process, a thin film transistor may be destroyed. In addition, a defect occurs due to fine fibers generated from the rubbing cloth, which hinders the improvement in production yield.

In order to overcome the problem of the rubbing process for the productivity improvement, a novel liquid crystal alignment process is designed, which is a liquid crystal alignment by using UV, namely, light (hereinafter, referred to as "optical alignment").

The optical alignment refers to a mechanism, in which a photosensitive group connected to the photoreactive polymer generates a photoreaction due to linearly polarized UV, and in this procedure, a main chain of the polymer is unidirectionally aligned, thereby forming a photopolymerizable liquid crystal alignment film in which the liquid crystals are aligned.

A representative example thereof is an optical alignment by photopolymerization, which is announced by M. Schadt, et al. (Jpn. J. Appl. Phys., Vol 31., 1992, 2155), Dae S. Kang, et al. (U.S. Pat. No. 5,464,669), and Yuriy Reznikov (Jpn. J. Appl. Phys. Vol. 34, 1995, L1000). In these patent documents and papers, polycinnamate-based polymers such as PVCN (poly(vinyl cinnamate)) and PVMC (poly(vinyl methoxycinnamate)) are generally used as the optical alignment polymers. In the case of performing the optical alignment, the cycloaddition reaction [2+2] of the double bond [2+2] of cinnamate by UV forms cyclobutane, and thus an anisotropic property is formed to unidirectionally align liquid crystal molecules, leading to the alignment of the liquid crystals.

In addition, Japanese Unexamined Patent Application Publication No. 11-1811127 discloses a polymer having a main chain such as acrylate and methacrylate and a side chain containing a photosensitive group such as a cinnamate group, and an alignment film comprising the same. Korean Patent Publication No. 2002-00068195 also discloses use of alignment film produced by using a polymethacryl-based polmer.

However, the aforementioned optical alignment polymers are disadvantageous in that thermal stability of the polymer main chain is reduced to deteriorate alignment stability or thermal stability of the alignment film, or the liquid crystal alignment becomes insufficient. For example, a polymer having an acryl-based main chain greatly reduces the stability of the alignment film due to the low thermal stability, and when the photosensitive group is restricted by the main chain, the group is difficult to rapidly react with the polarized light radiated to the alignment film, and thus liquid crystal alignment or alignment speed is deteriorated. The deterioration in liquid crystal alignment or alignment speed reduces the process efficiency. Further, the alignment of the liquid crystals is insufficient in the manufactured liquid crystal display, and thus there are problems in that a dichroic ratio becomes small and contrast degradation may occur.

SUMMARY OF THE INVENTION

Accordingly, the present invention provides a photoreactive polymer that shows excellent liquid crystal alignment and thermal stability, thereby being desirably used in an alignment film of a liquid crystal display device, and a compound having a photoreactive functional group that is used as a monomer for the preparation of the photoreactive polymer.

Further, the present invention provides an alignment film that comprises the photoreactive polymer as an optical alignment polymer to show excellent liquid crystal alignment and stability.

The present invention provides a compound having a photoreactive functional group, represented by the following Formula 1:

A-R                                       [Formula 1]

wherein A is a cyclic olefin-based ring, and R is one or more functional groups substituted in A, in which at least one is a radical of the following Chemical Formula 1a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 1a]

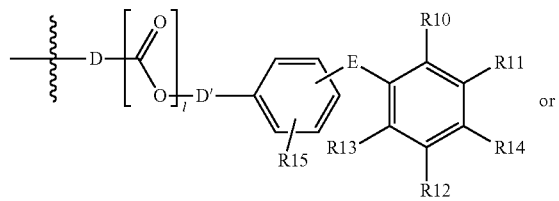

-continued

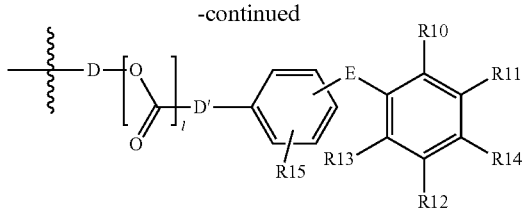

wherein l is 0 or 1, D and D' are each independently selected from the group consisting of a single bond, nitrogen, oxygen, sulfur, substituted or unsubstituted, linear or branched alkylene having 1 to 20 carbon atoms; substituted or unsubstituted cycloalkylene having 3 to 12 carbon atoms; substituted or unsubstituted, linear or branched alkylene oxide having 1 to 20 carbon atoms; and substituted or unsubstituted cycloalkylene oxide having 3 to 12 carbon atoms, E is

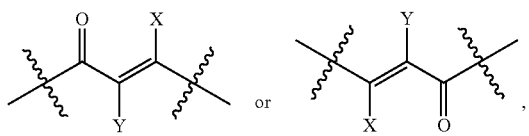

X and Y are each independently selected from the group consisting of hydrogen; halogen; cyano; and substituted or unsubstituted, linear or branched alkyl having 1 to 20 carbon atoms, and $R_{10}$, $R_{11}$, $R_{12}$, $R_{13}$, and $R_{14}$ are each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms, and $R_{15}$ is one or two substituent(s), and each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms.

Further, the present invention provides a photoreactive polymer comprising a repeating unit of the following Chemical Formula 1:

[Chemical Formula 1]

wherein m is 50 to 5000, A' is a cyclic olefin-based repeating unit, and R is the same as defined in Formula 1.

The photoreactive polymer may further comprise one or more repeating unit selected from the group consisting of the following Chemical Formulae 2 and 3:

[Chemical Formula 2]

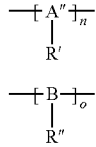

[Chemical Formula 3]

wherein n and o are each independently 50 to 5000, A" is a cyclic olefin-based repeating unit, B is an olefin-based repeating unit, R' is one or more functional groups substituted in A", in which at least one is a radical of the following Chemical Formula 2a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms, and R" is one or more functional groups substituted in B, and each independently selected from the group consisting of a radical of Chemical Formula 1a; a radical of Chemical Formula 2a; hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 2a]

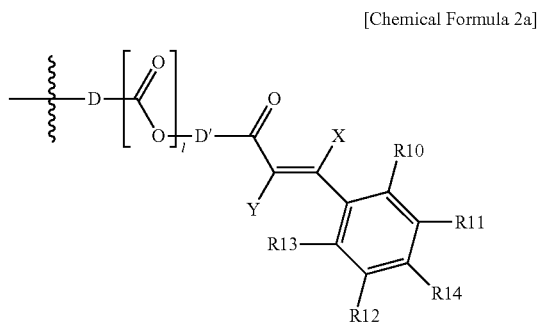

wherein l, D, D', X, Y, $R_{10}$, $R_{11}$, $R_{12}$, $R_{13}$, and $R_{14}$ are the same as defined in Chemical Formula 1a, and are the same as or different from those in Chemical Formula 1a.

Further, the present invention provides an alignment film comprising the photoreactive polymer.

DETAILED DESCRIPTION OF THE EMBODIMENTS

Figure 1:
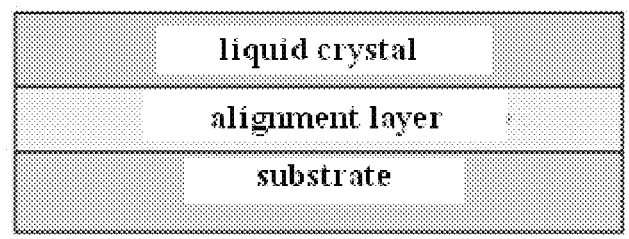
FIG. 1 illustrates an exemplary structure of the conventional alignment film.

Hereinafter, a photoreactive polymer according to one embodiment of the present invention, a compound having a photoreactive functional group used for the preparation thereof, and an alignment film comprising the photoreactive polymer will be described in more detail.

According to one embodiment of the present invention, a novel compound having a photoreactive functional group represented by the following Formula 1 is provided:

A-R  [Formula 1]

wherein A is a cyclic olefin-based ring, and R is one or more functional groups substituted in A, in which at least one is a radical of the following Chemical Formula 1a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 1a]

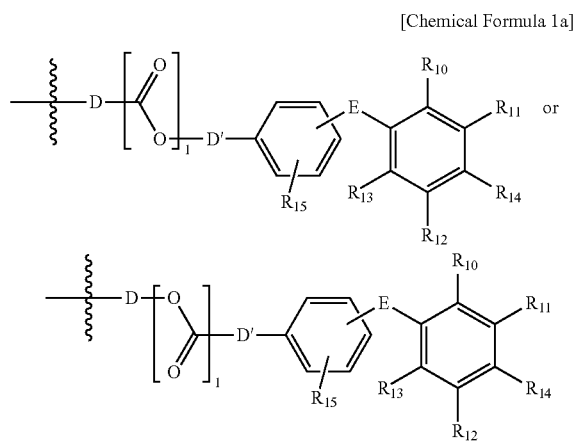

wherein l is 0 or 1, D and D' are each independently selected from the group consisting of a single bond, nitrogen, oxygen, sulfur, substituted or unsubstituted, linear or branched alkylene having 1 to 20 carbon atoms; substituted or unsubstituted cycloalkylene having 3 to 12 carbon atoms; substituted or unsubstituted, linear or branched alkylene oxide having 1 to 20 carbon atoms; and substituted or unsubstituted cycloalkylene oxide having 3 to 12 carbon atoms, E is

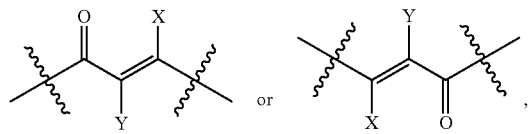

X and Y are each independently selected from the group consisting of hydrogen; halogen; cyano; and substituted or unsubstituted, linear or branched alkyl having 1 to 20 carbon atoms, and $R_{10}$, $R_{11}$, $R_{12}$, $R_{13}$, and $R_{14}$ are each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms, and $R_{15}$ is one or two substituent(s), and each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms.

The compound of Formula 1 may be used as a photoreactive compound as it is, or used to provide a photoreactive polymer having a specific structure through a polymerization method described below.

Therefore, according to another embodiment of the present invention, a photoreactive polymer having a specific structure is provided. The photoreactive polymer may include a repeating unit of the following Chemical Formula 1.

[Chemical Formula 1]

wherein m is 50 to 5000, A' is a cyclic olefin-based repeating unit, and R is the same as defined in Formula 1.

The photoreactive polymer may be a homopolymer containing the repeating unit of Chemical Formula 1 only, but may be a copolymer further containing one or more repeating units selected from the group consisting of the following Chemical Formulae 2 and 3, together with the repeating unit of Chemical Formula 1. In addition, as long as the properties of Chemical Formula 1 are not affected, other different repeating units may be further included:

[Chemical Formula 2]

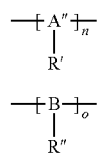

[Chemical Formula 3]

wherein n and o are each independently 50 to 5000, A" is a cyclic olefin-based repeating unit, B is an olefin-based repeating unit, R' is one or more functional groups substituted in A", in which at least one is a radical of the following Chemical Formula 2a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms, and R" is one or more functional groups substituted in B, and each independently selected from the group consisting of a radical of Chemical Formula 1a; a radical of Chemical Formula 2a; hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 2a]

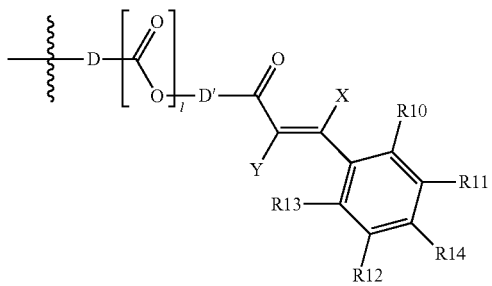

wherein l, D, D', X, Y, $R_{10}$, $R_{11}$, $R_{12}$, $R_{13}$, and $R_{14}$ are the same as defined in Chemical Formula 1a, and are the same as or different from those in Chemical Formula 1a.

The photoreactive polymer that can be obtained from the compound of Formula 1 essentially includes the cyclic olefin-based repeating unit of Chemical Formula 1, in which the repeating unit is structurally rigid and has a relatively high glass transition temperature (Tg) of 200° C. or higher, preferably 200 to 350° C., and thus the photoreactive polymer is able to show excellent thermal stability, compared to the known photoreactive polymers. Accordingly, the photoreactive polymer can be used to provide an alignment film showing excellent alignment stability and thermal stability.

Further, the repeating unit obtained by linking a chalcone or cinnamate structure showing photoreactivity to a cyclic olefin-based or olefin-based repeating unit (for example, the repeating unit of Chemical Formula 1, and selectively the repeating unit(s) of Chemical Formula 2 and/or 3) is included, and the double bond of the photoreactive functional groups is more easily broken to form a [2+2] bond. Therefore, the photoreactive polymer is able to show excellent photoreactivity, and the alignment film including the same is also able to show excellent liquid crystal alignment.

Additionally, the liquid crystal alignment speed can be controlled by varying the type or ratio of the repeating unit included in the photoreactive polymer or the type of various substituents substituted in each repeating unit. For example, if a strong electron donor group such as fluorine or nitro is linked to each repeating unit as a substituent, the double bond of the chalcone or cinnamate structure is more easily broken, and thus the photoreactive polymer can more quickly show photoreactivity and the liquid crystal alignment speed of the alignment film can be increased.

As described above, the photoreactive polymer can be used to provide an alignment film showing excellent stability and liquid crystal alignment and to control the liquid crystal alignment speed, thereby being very preferably applied as an optical alignment polymer in the alignment film of various liquid crystal display devices.

Hereinbelow, the compound of Formula 1 and the photoreactive polymer will be described in more detail.

The compound of Formula 1 may be, for example, a norbornene-based compound represented by the following Formula 1b:

[Formula 1b]

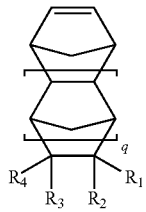

wherein q is an integer of 0 to 4, and at least one of $R_1$, $R_2$, $R_3$ and $R_4$ is a radical of Chemical Formula 1a, and the others are each independently hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

The norbornene-based compound is subjected to addition polymerization or ring-opening polymerization to obtain a representative photoreactive polymer belonging to the category of Chemical Formula 1, which will be described in more detail below. More specifically, the norbornene-based compound of Formula 1b is subjected to addition polymerization, thereby providing a photoreactive polymer including the norbornene-based repeating unit of the following Chemical Formula 1b, and is subjected to ring-opening polymerization, thereby providing a photoreactive polymer including the repeating unit of the following Chemical Formula 1c:

[Chemical Formula 1b]

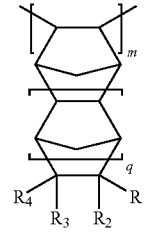

[Chemical Formula 1c]

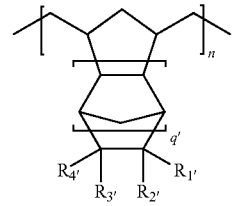

wherein m is 50 to 5000, q is an integer of 0 to 4, and at least one of $R_1$, $R_2$, $R_3$ and $R_4$ is a radical of Chemical Formula 1a and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

The norbornene-based repeating unit of Formula 1b or 1c is structurally rigid and has a high glass transition temperature, and thus the photoreactive polymer including the same is able to show more excellent thermal stability, and the alignment stability and thermal stability of the alignment film can be more improved. Further, binding of the repeating unit and the photoreactive functional group is properly controlled to maintain the excellent liquid crystal alignment of the alignment film.

However, it is also clear that the photoreactive polymer may include various cyclic olefin-based repeating units belonging to the category of Chemical Formula 1 in addition to those of Chemical Formula 1b and 1c.

Meanwhile, in the radical of Chemical Formula 1a or 2a which binds to each repeating unit of the photoreactive polymer, at least one of $R_{10}$, $R_{11}$, $R_{12}$, $R_{13}$, and $R_{14}$ may be halogen or halogen-substituted alkyl having 1 to 20 carbon atoms. More specifically, the halogen may be fluorine, chlorine, bromine, or iodine, and preferably fluorine.

As the halogen substituent binds to each repeating unit, the photoreactive polymer shows more excellent photoreactivity, and is included in the alignment film, thereby showing excellent liquid crystal alignment, which is possibly attributed to a strong compositional gradient in the alignment film that is caused by the halogen substituent. The compositional gradient means a distribution difference of binder resin and optical alignment polymer in the alignment film with respect to the distance from a base material. For example, when UV curing is performed to form the alignment film after applying a coating composition containing the binder resin and optical alignment polymer to the base material, a compositional gradient occurs so that more binder resins exist close to the base material and more optical alignment polymers exist far from the base material, or a reverse distribution may occur. However, if the photoreactive polymer includes a repeating unit having a halogen substituent (e.g., fluorine-containing substituent), a stronger compositional gradient may occur. For example, if the base material is highly polar, a repulsive force causes that more binder resins exist close to the base material and more photoreactive polymers exist far from the base material (e.g., with respect to the liquid crystals as in the structure of FIG. 1). Due to this phenomenon, a larger amount of optical alignment polymer (that is, the photoreactive polymer) may exist close to the liquid crystals, and thus the alignment film including the same is able to show more excellent liquid crystal alignment.

If the photoreactive polymer further includes the repeating unit of Chemical Formula 2, the repeating unit may be also various cyclic olefin-based repeating units, for example, a norbornene-based repeating unit represented by the following Chemical Formula 2b or 2c:

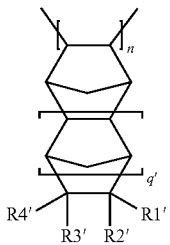

[Chemical Formula 2b]

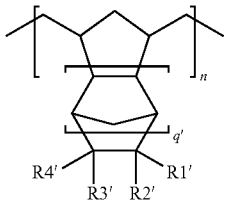

[Chemical Formula 2c]

wherein n is 50 to 5000, q' is an integer of 0 to 4, and at least one of $R_1'$, $R_2'$, $R_3'$ and $R_4'$ is a radical of Chemical Formula 2a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

As mentioned above, the norbornene-based repeating unit has a high glass transition temperature and is structurally rigid. Thus, as the repeating unit of Chemical Formula 2 is a norbornene-based repeating unit of Chemical Formula 2b or 2c, the photoreactive polymer and the alignment film including the repeating unit are able to show more excellent thermal stability, alignment stability or the like.

Meanwhile, if the photoreactive polymer further includes a repeating unit of Chemical Formula 3 together with the repeating unit of Chemical Formula 1, the repeating unit may be an olefin-based repeating unit represented by the following Chemical Formula 3a:

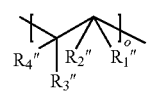

[Chemical Formula 3a]

wherein o is 50 to 5000, and $R_1''$, $R_2''$, $R_3''$ and $R_4''$ are each independently selected from the group consisting of a radical of Chemical Formula 1a; a radical of Chemical Formula 2a; hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

The olefin-based repeating unit may or may not include a photoreactive functional group, and may be a non-cyclic olefin-based repeating unit, as distinct from the aforementioned cyclic olefin-based repeating unit. The physical properties of the photoreactive polymer and the alignment film including the same, for example, photoreactivity, liquid crystal alignment, alignment speed or stability can be easily controlled by adjusting a content ratio of the repeating unit.

Meanwhile, if the photoreactive polymer is a copolymer including the repeating unit(s) of Chemical Formula (e) 2 and/or 3 together with the repeating unit of Chemical Formula 1, the photoreactive polymer easily controls the physical properties of the alignment film including the same by adjusting a ratio of each repeating unit. Therefore, the ratio of the repeating units of Chemical Formulae 1 to 3 may be easily determined by those skilled in the art.

However, considering the appropriate physical properties to be satisfied by the photoreactive polymer and the alignment film, each of the repeating units of Chemical Formulae 2 and 3 may be included at a ratio of 0.1-2.0 mol and 0.2-2.0 mol, and preferably 0.5-2.0 mol and 0.5-2.0 mol, based on 1 mol of the repeating unit of Chemical Formula 1.

In each repeating unit included in the compound belonging to the category of Formula 1 and the photoreactive polymer, a photoreactive functional group such as the radical of Chemical Formula 1a or 2a may properly bind to the position corresponding to $R_1$, $R_1'$ or $R_1''$.

Further, in each repeating unit included in the compound of Formula 1 and the photoreactive polymer, the substituted or unsubstituted aryl having 6 to 40 carbon atoms; or the hetero aryl having 6 to 40 carbon atoms that includes Group 14, 15 or 16 hetero elements may be selected from the functional groups listed as follows, or may be other aryls or hetero aryls:

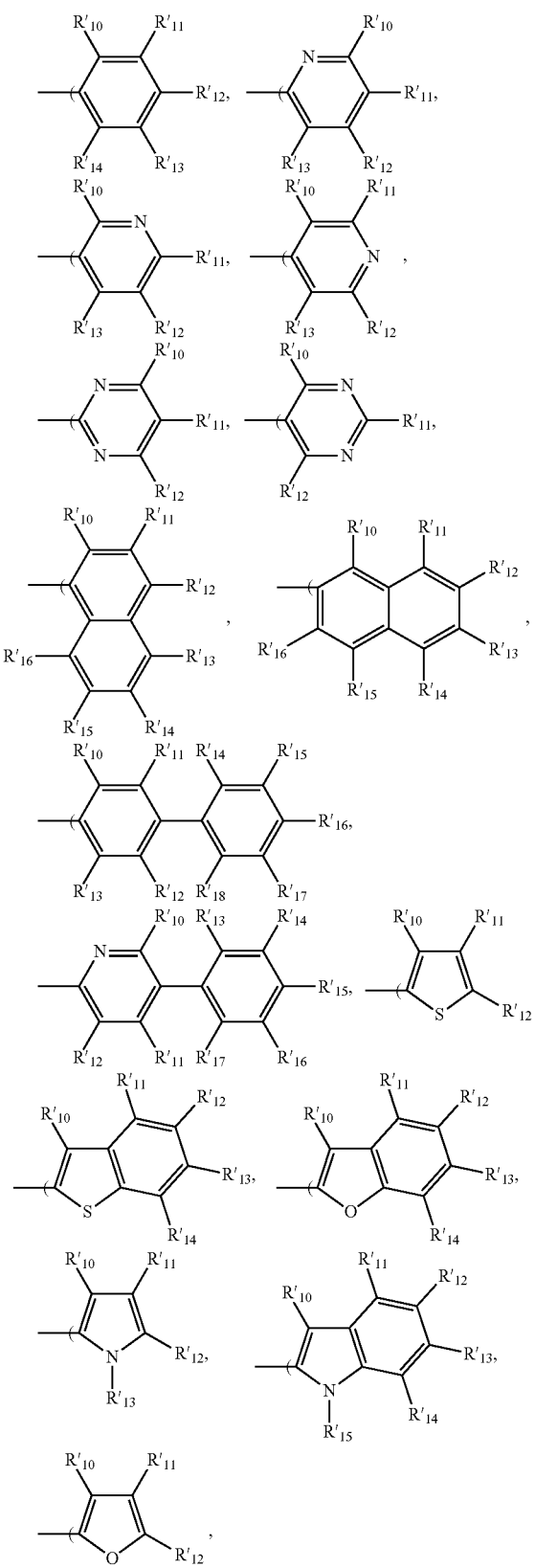

wherein R'$_{10}$ to R'$_{18}$ are each independently selected from the group consisting of substituted or unsubstituted, linear or branched alkyl having 1 to 20 carbon atoms, substituted or unsubstituted alkoxy having 1 to 20 carbon atoms, substituted or unsubstituted aryloxy having 6 to 30 carbon atoms, and substituted or unsubstituted aryl having 6 to 40 carbon atoms.

Meanwhile, as described above, the photoreactive polymer may further include an additional repeating unit in addition to these repeating units, and may be prepared into a variety of copolymers. In connection with this, the content ratio of additional repeating unit is also determined by those skilled in the art, considering properties of the desired photoreactive polymer.

The photoreactive polymer may have a weight-average molecular weight of 10000 to 1000000, and preferably 20000 to 500000. Accordingly, the photoreactive polymer is properly included in the coating composition for the production of alignment film, so that it shows excellent coating properties and the alignment film formed therefrom is also able to show excellent liquid crystal alignment or the like.

Meanwhile, in the structure of the above described compound of Formula 1 and photoreactive polymer, the detailed definition of each substituent is as follows:

First, the term "alkyl" means a linear or branched, saturated monovalent hydrocarbon of 1 to 20 carbon atoms, preferably 1 to 10 carbon atoms, and more preferably 1 to 6 carbon atoms. The alkyl group may encompass those that are unsubstituted or further substituted with a specific substituent described below. Examples of the alkyl group may include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl or the like.

The term "alkenyl group" means a linear or branched, monovalent hydrocarbon of 2' to 20 carbon atoms, preferably 2 to 10 carbon atoms, and more preferably 2 to 6 carbon atoms, which includes one or more carbon-carbon double bonds. The alkenyl group may be bounded through a carbon atom including a carbon-carbon double bond or a saturated carbon atom. The alkenyl group may encompass those that are unsubstituted or further substituted with a specific substituent described below. Examples of the alkenyl group include ethenyl, 1-prophenyl, 2-prophenyl, 2-butenyl, 3-butenyl, pentenyl, 5-hexenyl, dodecenyl or the like.

The term "cycloalkyl group" means a saturated or unsaturated non-aromatic monovalent monocyclic, bicyclic, or tricyclic hydrocarbon of 3 to 12 cyclic carbon atoms, and may encompass those that are further substituted with a specific substituent described below. Examples of the cycloalkyl group include cyclopropyl, cyclobutyl, cyclopentyl, cyclopentenyl, cyclohexyl, cyclohexenyl, cycloheptyl, cyclooctyl, decahydronaphtalenyl, adamantyl, norbornyl (e.g., bicyclo [2,2,1]hept-5-enyl) or the like.

The term "aryl" means a monovalent monocyclic, bicyclic, or tricyclic aromatic hydrocarbon having 6 to 40, preferably 6 to 12 cyclic atoms, and may encompass those that are further substituted with a specific substituent described below. Examples of the aryl group may include phenyl, naphthalenyl, fluorenyl or the like.

The term "alkoxyaryl" means that one or more hydrogen atoms of the aryl group defined as described above are substituted with the alkoxy group. Examples of the alkoxyaryl group may include methoxyphenyl, ethoxyphenyl, propoxyphenyl, butoxyphenyl, pentoxyphenyl, heptoxyphenyl, heptoxy, octoxy, nanoxy, methoxybiphenyl, methoxynaphthalenyl, methoxyfluorenyl, methoxyanthracenyl or the like.

The term "aralkyl" means that one or more hydrogen atoms of the alkyl group defined as described above are substituted with the aryl group, and may encompass those that are further substituted with a specific substituent described below. Examples of the aralkyl may include benzyl, benzhydril, tritile or the like.

The term "alkynyl" means a linear or branched, monovalent hydrocarbon of 2 to 20 carbon atoms, preferably 2 to 10 carbon atoms, and more preferably 2 to 6 carbon atoms, which includes one or more carbon-carbon triple bonds. The alkynyl group may be bound through a carbon atom including a carbon-carbon triple bond or a saturated carbon atom. The alkynyl group may encompass those that are further substituted with a specific substituent described below. Examples of the alkynyl group may include ethynyl, propynyl or the like.

The term "alkylene" means a linear or branched, saturated divalent hydrocarbon of 1 to 20 carbon atoms, preferably 1 to 10 carbon atoms, and more preferably 1 to 6 carbon atoms. The alkylene group may encompass those that are further substituted with a specific substituent described below. Examples of the alkylene group may include methylene, ethylene, propylene, butylene, hexylene or the like.

The term "cycloalkylene" means a saturated or unsaturated nonaromatic divalent monocyclic, bicyclic or tricyclic hydrocarbon having 3 to 12 cyclic carbons, and may encompass those that are further substituted with a specific substituent described below. Examples of the cycloalkylene may include cyclopropylene, cyclobutylene or the like.

The "alkyl oxide" or "cycloalkyl oxide" means a monovalent moiety, in which one or more hydrogen atoms of the alkyl or cycloalkyl group defined as described above are substituted with oxygen. Examples thereof may include ethyl oxide, propyl oxide, cyclohexyl oxide or the like.

The "alkylene oxide" or "cycloalkylene oxide" means a divalent moiety, in which one or more hydrogen atoms of the alkylene or cycloalkylene group defined as described above are substituted with oxygen. Examples thereof may include ethylene oxide, propylene oxide, cyclohexylene oxide or the like.

The above described, "those substituted or unsubstituted with substituents" means that they encompass those further substituted with a specific substituent as well as each substituent itself. Herein, examples of the substituent further substituted in each substituent may include halogen, alkyl, alkenyl, alkynyl, haloalkyl, haloalkenyl, haloalkynyl, aryl, haloaryl, aralkyl, haloaralkyl, alkoxy, halo haloalkoxy, carbonyloxy, halocarbonyloxy, aryloxy, haloaryloxy, sillyl or siloxy or the like.

Meanwhile, the above described compound of Formula 1 may be prepared by a typical process, in which a compound corresponding to the photoreactive functional group —R is prepared from the known compound, and then bound to the cyclic olefin-based ring A. Specific examples thereof are described in Examples hereinbelow.

The photoreactive polymer may be prepared by different polymerization methods according to the type of each repeating unit. For example, the polymer including the norbornene-based repeating unit of Chemical Formula 1b as the repeating unit of Chemical Formula 1 or including the norbornene-based repeating unit of Chemical Formula 2b as the repeating unit of Chemical Formula 2 together with the norbornene-based repeating unit of Chemical Formula 1b as the repeating unit of Chemical Formula 1 may be prepared by addition polymerization of one or more of the compound of Formula 1 corresponding to these repeating units (e.g., the compound of Formula 1b) as a monomer. At this time, the addition polymerization may be performed in the presence of a catalyst composition containing a Group 10 transition metal precatalyst and a cocatalyst.

The addition polymerization may be performed at a temperature of 10° C. to 200° C. If the reaction temperature is lower than 10° C., there is a problem in that activity of polymerization is very low. If the reaction temperature is higher than 200° C., the catalyst is decomposed, which is undesirable.

In addition, the cocatalyst may include one or more selected from the group consisting of a first co-catalyst for providing a Lewis base capable of weakly coordinating with metal of the precatalyst; and a second cocatalyst for providing a compound containing a Group 15 electron donor ligand. Preferably, the cocatalyst may be a catalytic mixture that includes the first cocatalyst for providing a Lewis base, and optionally the second cocatalyst for providing a compound containing a neutral Group 15 electron donor ligand.

In this regard, the catalytic mixture may include 1 to 1000 mol of the first cocatalyst, and 1 to 1000 mol of the second cocatalyst, based on 1 mol of the precatalyst. If the content of the first or second cocatalyst is too low, activation of the catalyst may not be properly achieved, and if the content is too high, the catalytic activity may be reduced.

A compound having the Lewis base functional group, which easily participates in a Lewis acid-base reaction to be separated from a core metal, may be used as the precatalyst having Group 10 transition metal so that the Lewis base is easily separated by the first cocatalyst to convert the central transition metal into the catalytic active species. It is exemplified by [(Allyl) Pd(Cl)]$_2$(Allylpalladiumchloride dimer), (CH$_3$CO$_2$)$_2$Pd [Palladium(II)acetate], [CH$_3$COCH=C(O—)CH$_3$]$_2$Pd [Palladium(II)acetylacetonate], NiBr(NP(CH$_3$)$_3$)$_4$, [PdCl(NB)O(CH$_3$)]$_2$ or the like.

Moreover, the first cocatalyst for providing the Lewis base capable of weakly coordinating with metal of the precatalyst may include a compound, which easily reacts with the Lewis base to form vacancies in the transition metal and which weakly coordinates with the transition metal compound, in order to stabilize the transition metal or another compound for providing this. It is exemplified by Borane such as B(C$_6$F$_5$)$_3$, borate such as dimethylanilinium tetrakis(pentafluorophenyl)borate, alkyl aluminum such as methyl aluminoxane or Al(C$_2$H$_5$)$_3$, or transition metal halide such as AgSbF$_6$.

The second cocatalyst for providing a compound containing a neutral Group 15 electron donor ligand may be alkyl phosphine, cycloalkyl phosphine or phenyl phosphine.

Further, the first cocatalyst and the second cocatalyst may be used separately, or these cocatalysts may be prepared into a salt, and used as a compound activating the catalyst. It is exemplified by a compound prepared by an ionic bond of alkyl phosphine and borane compound.

Meanwhile, the polymer including the norbornene-based repeating unit of Chemical Formula 1c as the repeating unit of Chemical Formula 1 or including the norbornene-based repeating unit of Chemical Formula 2c as the repeating unit of Chemical Formula 2 together with the norbornene-based repeating unit of Chemical Formula 1c as the repeating unit of Chemical Formula 1 may be prepared by ring-opening polymerization of the compound of Formula 1 corresponding to these repeating units (e.g., the compound of Formula 1b) as a monomer.

At this time, the ring-opening polymerization may be performed in the presence of a catalytic mixture consisting of a precatalyst having a transition metal of Group 4 (e.g., Ti, Zr, Hf), Group 6 (e.g., Mo, W), or Group 8 (e.g., Ru, Os), a cocatalyst for providing the Lewis base capable of weakly coordinating with metal of the precatalyst, and optionally, a neutral Group 15 or 16 activator capable of improving the activity of the metal of the precatalyst. In the presence of the catalytic mixture, the polymerization may be also performed at a temperature of 10° C. to 200° C. by addition of 1-100 mol % of a linear alkene capable of adjusting a molecular weight such as 1-alkene and 2-alkene, based on the monomer. Subsequently, addition of hydrogens to the double bonds remaining in the main chain may be performed at a temperature of 10° C. to 250° C. by addition of 1 to 30% by weight of the catalyst having a transition metal of Group 4 (e.g., Ti, Zr), or Group 8 to 10 (e.g., Ru, Ni, Pd), based on the monomer.

The photoreactive polymer including the olefin-based repeating unit of Chemical Formula 3 together with the cyclic olefin-based repeating units of Chemical Formula 1 and/or 2 may be obtained by performing polymerization in the presence of a catalyst composition containing a precatalyst having a Group 4 transition metal such as zirconium and titanium and a cocatalyst, or in the presence of an azo or peroxide compound. However, the polymerization conditions of olefin-based monomers are well known to those skilled in the art, and thus a detail description thereof will be omitted.

In addition to the above described methods, various preparation methods may be applied to obtain the photoreactive polymer of Chemical Formula 1 according to the types of monomers and repeating units, and the preparation methods thereof according to the type of monomers are well known to those skilled in the art.

Meanwhile, according to still another embodiment of the present invention, an alignment film comprising the above described photoreactive polymer is provided. The alignment film may also include a film type as well as a thin layer type.

The alignment film may be produced using the components and preparation methods well known to those skilled in the art, excluding that the alignment film includes the above described photoreactive polymer as an optical alignment polymer.

For example, the photoreactive polymer, a binder resin and a photoinitiator are mixed and dissolved in an organic solvent to prepare a coating composition, and then the coating composition is applied to a base material, and UV curing is performed to form the alignment film.

At this time, an acrylate-based resin may be used as the binder resin, and more particularly, pentaerythritol triacrylate, dipentaerythritol hexaacrylate, trimethylolpropane triacrylate, tris(2-acryloyloxyethyl) isocyanurate or the like may be used.

Further, typical photoinitiators that are known to be used in the alignment film may be used as the photoinitiator without limitation, for example, a photoinitiator under the trade name of Irgacure 907 or 819.

Toluene, anisole, chlorobenzene, dichloroethane, cyclohexane, cyclopentane, propyleneglycolmethylether acetate or the like may be used as the organic solvent. The above described, photoreactive norbornene-based copolymer shows excellent solubility to various organic solvents, and thus other organic solvents may be used without limitation.

In the coating composition, the solid containing the photoreactive polymer, the binder resin and the photoinitiator may be used at a concentration of 1 to 15% by weight. In order to cast the alignment film in a film type, a preferred concentration is 10 to 15% by weight, and in order to form the alignment film in a thin layer type, a preferred concentration is 1 to 5% by weight.

As shown in FIG. 1, the produced alignment film may be formed between the base material and the liquid crystals, and functions to align the liquid crystals. In connection with this, a base material containing a cyclic polymer, an acrylic polymer, or a cellulose polymer may be used as the base material, and the coating composition is applied to the base material by various methods such as bar coating, spin coating, and blade coating, and then UV curing is performed to form the alignment film.

As described above, the present invention provides a novel compound having a photoreactive functional group, and a specific photoreactive polymer produced from the same. The photoreactive polymer comprises a predetermined cyclic olefin-based repeating unit to show high glass transition temperature and excellent thermal stability, thereby providing an alignment film with excellent alignment stability and thermal stability.

Further, the photoreactive polymer and the alignment film comprising the same are able to show excellent liquid crystal alignment and alignment speed, and also control photoreaction rate by UV and liquid crystal alignment speed according to various repeating units or substituents.

Therefore, the photoreactive polymer can be preferably used as an optical alignment polymer in the alignment film that is applied to various liquid crystal display devices, and the alignment film comprising the photoreactive polymer is able to show excellent properties.

EXAMPLES

Hereinafter, the preferred Examples are provided for better understanding. However, these Examples are for illustrative purposes only, and the invention is not intended to be limited by these Examples.

In the examples as described below, all operations for handling compounds which were sensitive to air or water were conducted using a standard Schlenk technique or a dry box technique. A nuclear magnetic resonance (NMR) spectrum was obtained using a Bruker 300 spectrometer. In connection with this, $^1$H NMR was measured at 300 MHz and $^{13}$C NMR was measured at 75 MHz. A molecular weight and a molecular weight distribution of a polymer prepared by ring-opening addition polymerization were measured using GPC (gel permeation chromatography). In connection with this, a polystyrene sample was used as a standard.

Toluene was purified by distillation from potassium/benzophenone, and dichloromethane was purified by distillation from $CaH_2$.

Preparation Example 1-1

Preparation of
(E)-4-(3-(4-fluorophenyl)acryloyl)benzoic acid

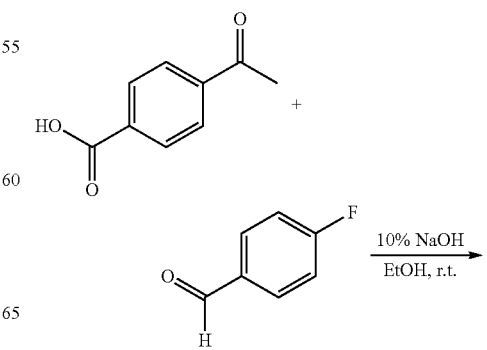

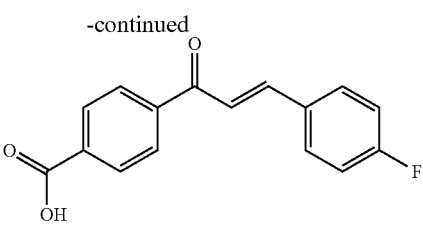

30 g of 4-acetylbenzoic acid (0.1827 mol, 1.0 eq.) and 4-fluorobenzaldehyde dissolved in 100 ml of ethanol were slowly added to 100 ml of 10% sodium hydroxide (0.2500 mol, 1.4 eq.) in a 1 L round bottomed flask. A clear yellow mixed solution was stirred at room temperature for 4 hrs.

When the reaction was completed, the mixed solution was cooled to 5° C. or below, and then added to 200 ml of water. 2 N HCl was added until pH 2.00.

When a light yellow solid was precipitated, the solid was obtained by filtration, and then washed with water 2-3 times, and dried under reduced pressure to obtain 48.1 g of (E)-4-(3-(4-fluorophenyl)acryloyl)benzoic acid.

Preparation Example 1-2

Preparation of (E)-bicyclo[2.2.1]hep-5-en-2-ylmethyl 4-(3-(4-fluorophenyl)acryloyl)benzoate

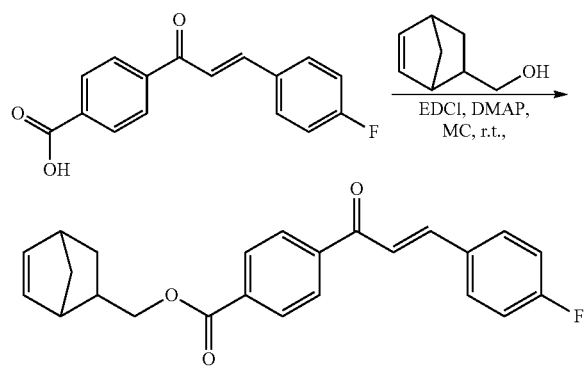

48 g (0.17 mol) of the compound prepared in Preparation Example 1-1 was dissolved in 400 ml of methylene chloride in a 1 L round bottomed flask, and then 37.45 g (0.19 mol, 1.1 eq.) of EDCl was added thereto.

21.5 ml of 5-norbornene-2-methanol (0.17 mol, 1.0 eq.) and 2.17 g (0.1 eq.) of DMAP were added to the solution at room temperature, and then stirred for 24 hrs. It was found that white precipitates gradually turned a clear yellow solution.

When the reaction was completed, 100 ml of methylene chloride was added to the reaction solution, and washed with 500 ml of saturated NaHCO$_3$, 500 ml of water, and then 500 ml of brine. The washed, methylene chloride mixture was dried over magnesium sulfate. After filtration, the solution was concentrated to obtain a yellow solid compound. Ethanol was added thereto, stirred, and then filtered.

1 L of water and 3 L of methylene chloride were added to 40 g of the yellow compound, and the methylene chloride solution was only separated. The solution was dried over magnesium sulfate, and concentrated to obtain a yellow compound.

Figure 2:
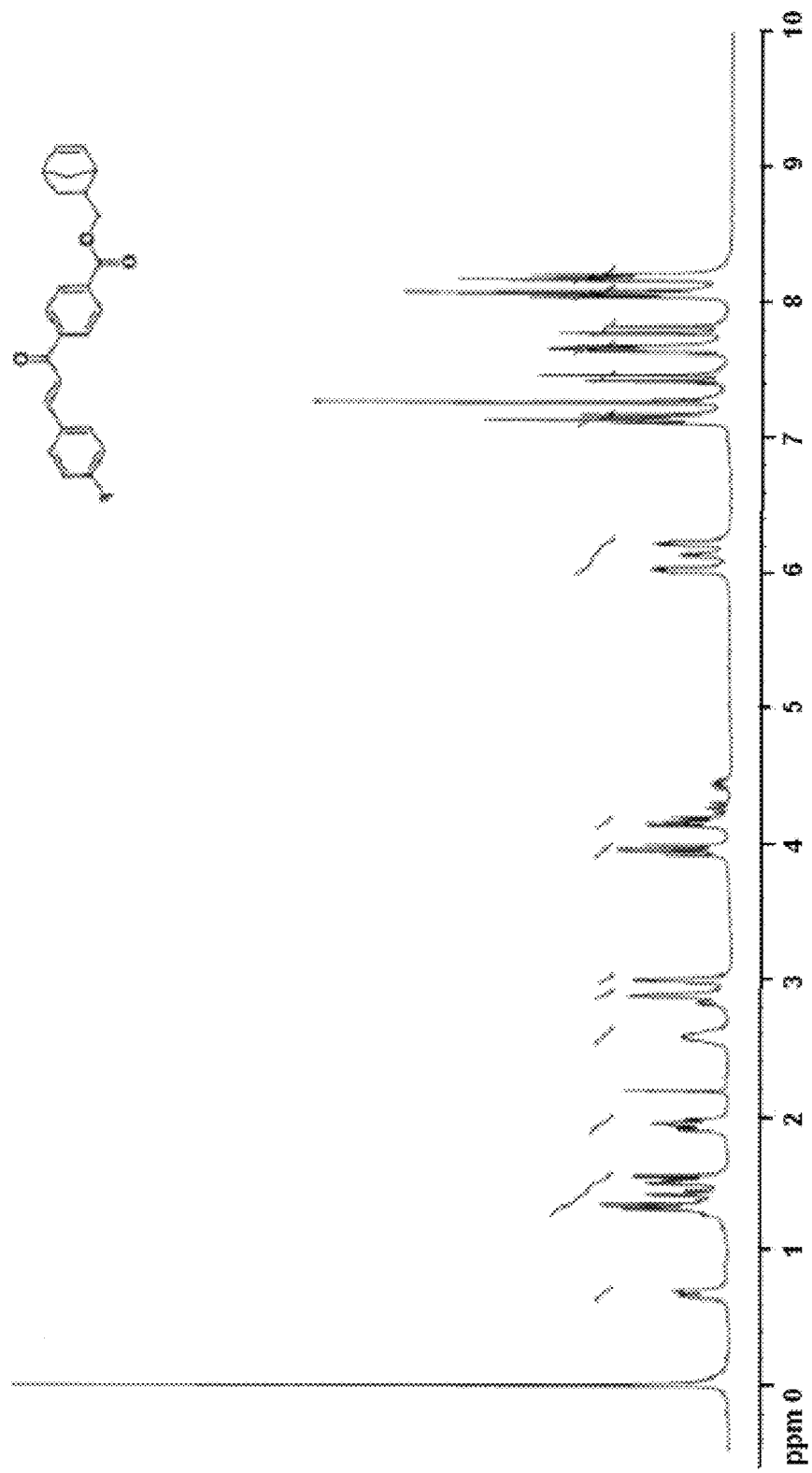
FIG. 2 is NMR data of the compound obtained in Preparation Example 1-2.

The obtained yellow compound was purified by column chromatography. 31.2 g of a final compound (yield: 46.7%) was obtained using hexane:ethyl acetate=5:1. NMR of the final compound was shown in FIG. 2.

Preparation Example 2

Preparation of (E)-bicyclo[2.2.1]hep-5-en-2-ylmethyl 3-(3-(4-fluorophenyl)acryloyl)benzoate

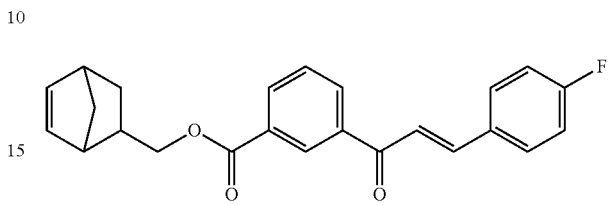

Figure 3:
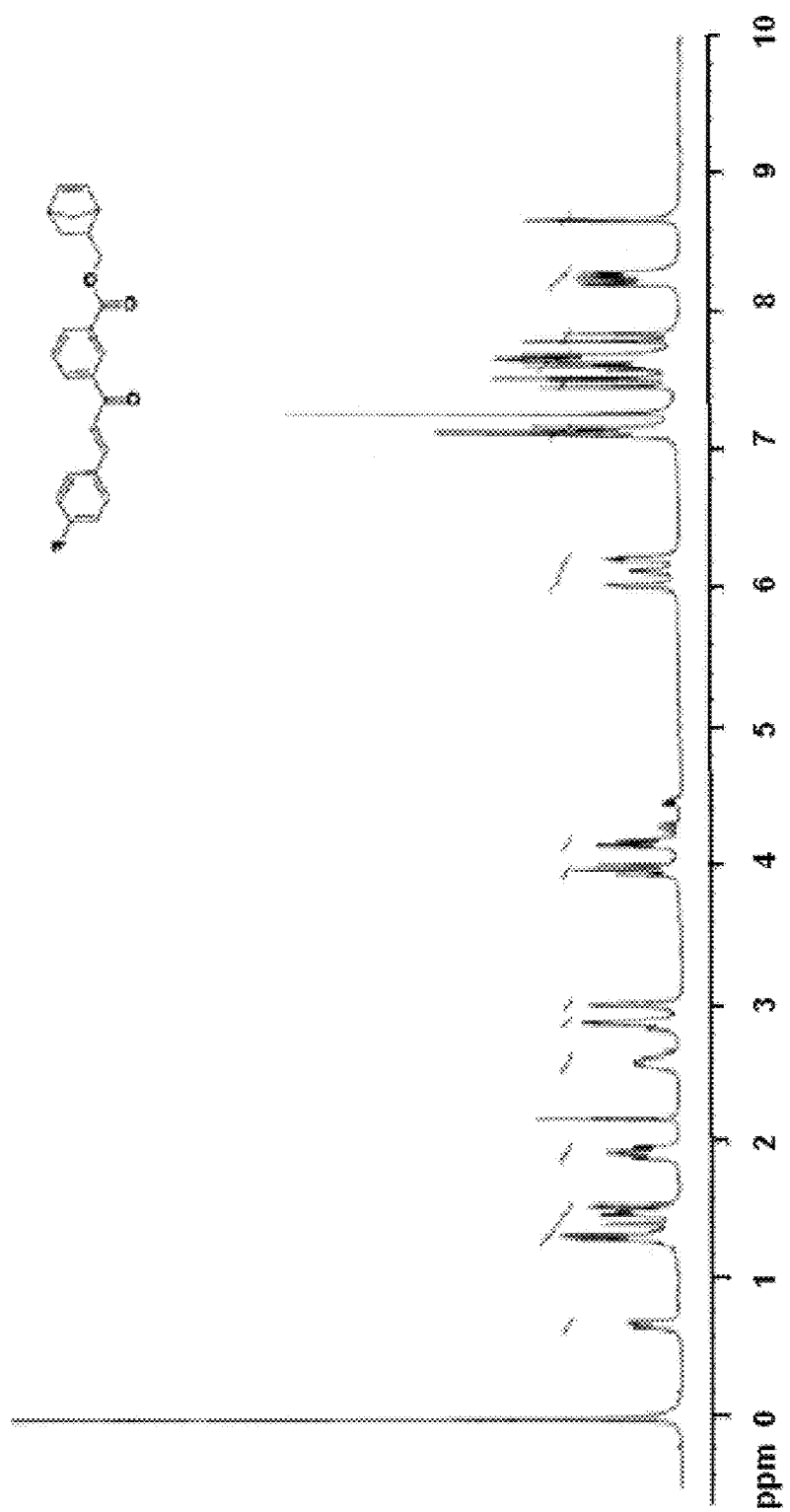
FIG. 3 is NMR data of the compound obtained in Preparation Example 2.

(E)-3-(3-(4-fluorophenyl)acryloyl)benzoic acid was prepared in the same manner as in Preparation Example 1-1, except that 3-acetyl benzoic acid was used instead of 4-acetyl benzoic acid in Preparation Example 1-1. The reaction was performed in the same manner as in Preparation Example 1-2 to obtain 31.0 g of a final compound, (E)-bicyclo[2.2.1] hept-5-en-2-ylmethyl 3-(3-(4-fluorophenyl)acryloyl)benzoate (yield: 46.5%). NMR of the final compound was shown in FIG. 3.

Example 1

Polymerization of

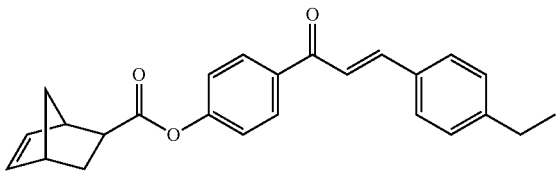 [SMILES: CCc1ccc(/C=C/C(=O)c2ccc(OC(=O)C3CC4C=CC3C4)cc2)cc1]

1.1 g (3 mmol) of

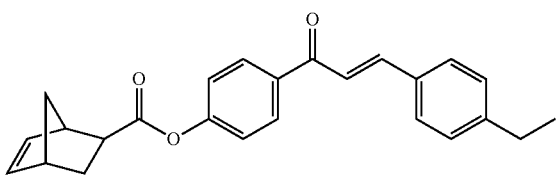 [SMILES: CCc1ccc(/C=C/C(=O)c2ccc(OC(=O)C3CC4C=CC3C4)cc2)cc1]

as a monomer and 3 ml of purified toluene as a solvent were put into a 250 ml schlenk flask. 6.73 mg of Pd(OAc)$_2$ dissolved in 1 ml of dichloromethane and 7.76 mg of tricyclohexylphosphine as a catalyst and 6.53 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 0.88 g of a polymer (Mw=131,000, PDI=3.7, yield=81%).

Example 2

Polymerization of

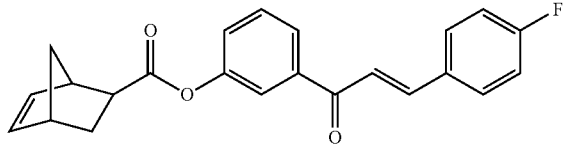 [SMILES: O=C(/C=C/c1ccc(F)cc1)c1cccc(OC(=O)C2CC3C=CC2C3)c1]

1.1 g (3 mmol) of

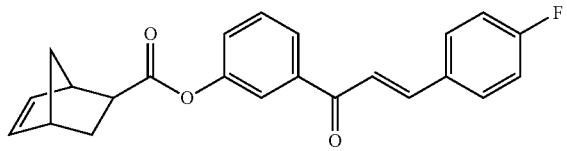 [SMILES: O=C(/C=C/c1ccc(F)cc1)c1cccc(OC(=O)C2CC3C=CC2C3)c1]

as a monomer and 3 ml of purified toluene as a solvent were put into a 250 ml schlenk flask. 6.73 mg of Pd(OAc)$_2$ dissolved in 1 ml of dichloromethane and 7.76 mg of tricyclohexylphosphine as a catalyst and 6.53 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 1.0 g of a polymer (Mw=153,000, PDI=3.9, yield=92%).

Example 3

Polymerization of

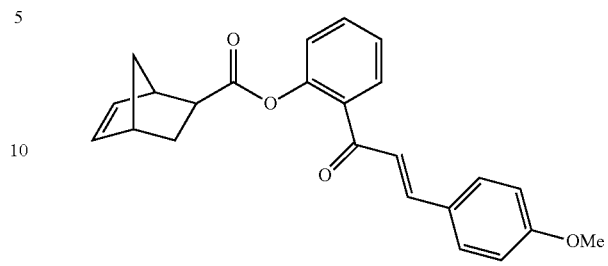

1.1 g (3 mmol) of

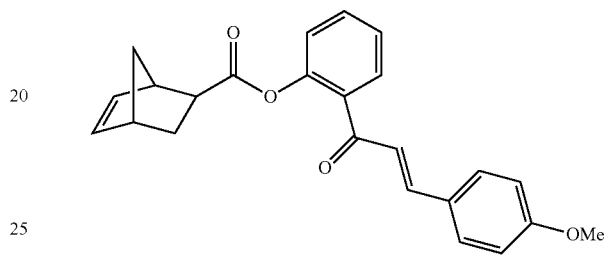

as a monomer and 3 ml of purified toluene as a solvent were put into a 250 ml schlenk flask. 6.73 mg of Pd(OAc)$_2$ dissolved in 1 ml of dichloromethane and 7.76 mg of tricyclohexylphosphine as a catalyst and 6.53 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 0.82 g of a polymer (Mw=83,000, PDI=2.5, yield=75%).

Example 4

Polymerization of

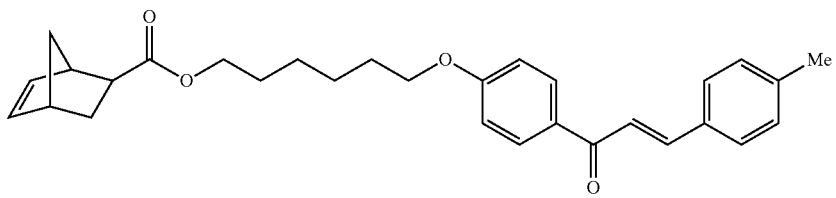 [SMILES: Cc1ccc(/C=C/C(=O)c2ccc(OCCCCCCOC(=O)C3CC4C=CC3C4)cc2)cc1]

1.39 g (3 mmol) of

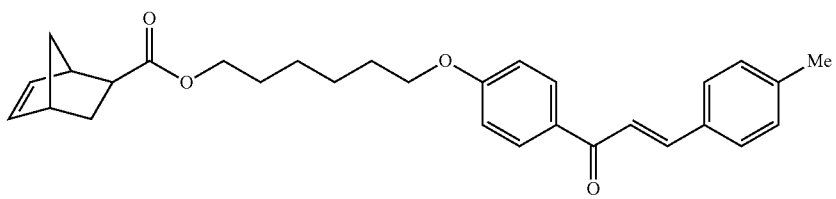 [SMILES: Cc1ccc(/C=C/C(=O)c2ccc(OCCCCCCOC(=O)C3CC4C=CC3C4)cc2)cc1]

as a monomer and 3 ml of purified toluene as a solvent were put into a 250 ml schlenk flask. 6.73 mg of Pd(OAc)₂ dissolved in 1 ml of dichloromethane and 7.76 mg of tricyclohexylphosphine as a catalyst and 6.53 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 0.88 g of a polymer (Mw=148,000, PDI=3.7, yield=82%).

Example 5

Polymerization of

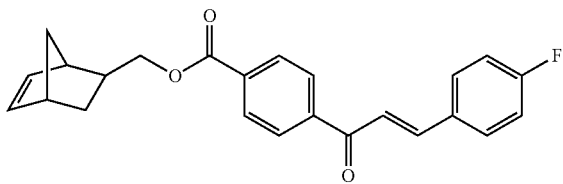 [SMILES: O=C(/C=C/c1ccc(F)cc1)c1ccc(C(=O)OCC2CC3C=CC2C3)cc1]

2.26 g (6 mmol) of

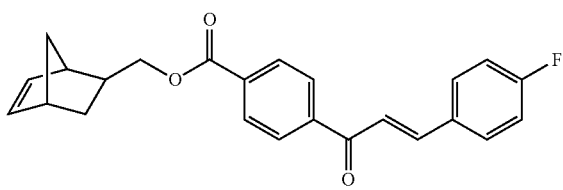 [SMILES: O=C(/C=C/c1ccc(F)cc1)c1ccc(C(=O)OCC2CC3C=CC2C3)cc1]

as a monomer and 6 ml of purified toluene as a solvent were put into a 250 ml schlenk flask. 13.46 mg of Pd(OAc)₂ dissolved in 1 ml of dichloromethane and 15.52 mg of tricyclohexylphosphine as a catalyst and 13.06 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 1.6 g of a polymer (Mw=185,000, PDI=4.2, yield=71%).

Example 6

Polymerization of

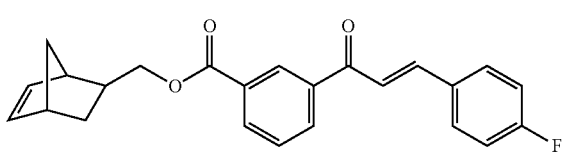 [SMILES: O=C(/C=C/c1ccc(F)cc1)c1cccc(C(=O)OCC2CC3C=CC2C3)c1]

2.26 g (6 mmol) of

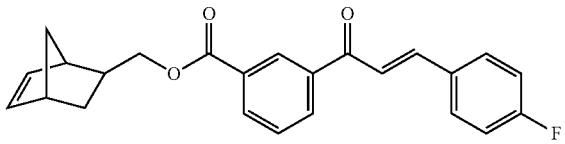 [SMILES: O=C(/C=C/c1ccc(F)cc1)c1cccc(C(=O)OCC2CC3C=CC2C3)c1]

as a monomer and 6 ml of purified toluene as a solvent were put into a 250 ml schlenk flask. 13.46 mg of Pd(OAc)₂ dissolved in 1 ml of dichloromethane and 15.52 mg of tricyclohexylphosphine as a catalyst and 13.06 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 1.7 g of a polymer (Mw=205,000, PDI=4.2, yield=75%).

Example 7

Copolymerization of

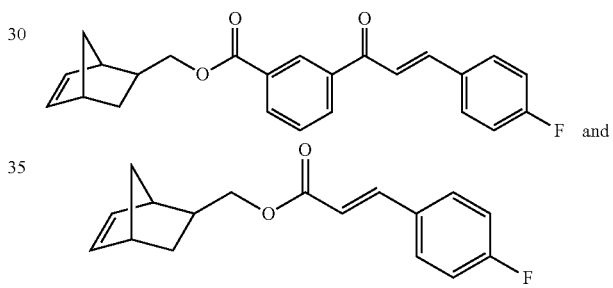 and 2.26 g (6 mmol) of

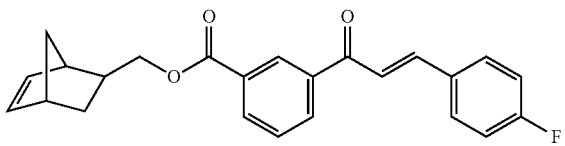 [SMILES: O=C(/C=C/c1ccc(F)cc1)c1cccc(C(=O)OCC2CC3C=CC2C3)c1]

and 1.63 g (6 mmol) of

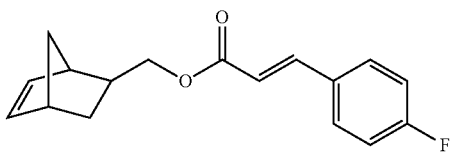 [SMILES: O=C(/C=C/c1ccc(F)cc1)OCC1CC2C=CC1C2]

as a monomer and 10 ml of purified toluene as a solvent were put into a 250 ml schlenk flask. 26.9 mg of Pd(OAc)₂ dissolved in 1 ml of dichloromethane and 31.04 mg of tricyclohexylphosphine as a catalyst and 26.1 mg of dimethylanilinium tetrakis(pentafluorophenyl)borate as a cocatalyst were put into the flask, and the reaction was performed at 90° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 3.57 g of a polymer (Mw=225,000, PDI=4.2, yield=92%).

Example 8

Copolymerization of

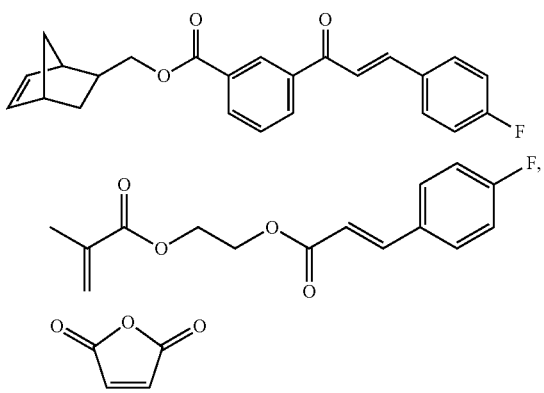

6.9 g (25 mmol) of

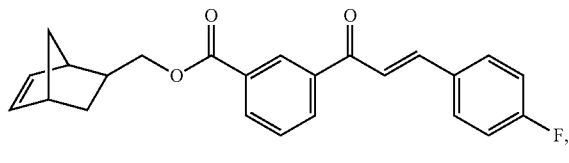 [SMILES: O=C(/C=C/c1ccc(F)cc1)c1cccc(C(=O)OCC2CC3C=CC2C3)c1]

and 1.22 g (12.5 mmol) of

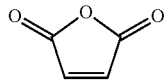

as a monomer and 40 ml of purified toluene as a solvent were put into a 250 ml schlenk flask. 25 mg (0.1 mmol) of V65 as an initiator was put into the flask, and the reaction was performed at 65° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 5.46 g of a polymer (Mw=52,000, PDI=4.4, yield=43%).

Example 9

Copolymerization of

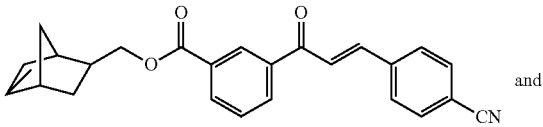

9.56 g (25 mmol) of

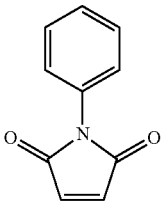

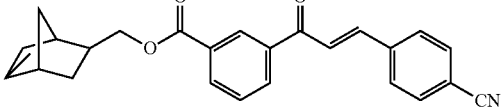

and 4.33 g (25 mmol) of

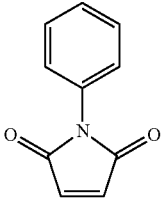 [SMILES: O=C1C=CC(=O)N1c1ccccc1]

as a monomer and 40 ml of purified toluene as a solvent were put into a 250 ml schlenk flask. 25 mg (0.1 mmol) of V65 as an initiator was put into the flask, and the reaction was performed at 65° C. for 18 hrs under stirring.

After the reaction for 18 hrs, the reactants were added to an excessive amount of ethanol to obtain a white polymer precipitate. The precipitate was filtered using a glass funnel, and the recovered polymer was dried in a vacuum oven at 60° C. for 24 hrs to obtain 5.7 g of a polymer (Mw=79,000, PDI=5.2, yield=41%).

Preparation Example 1

Production of Alignment Film Using Polymer of Example 2

The photoreactive polymer that was synthesized using the monomer

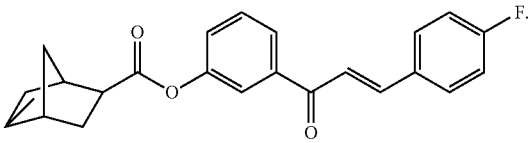 [SMILES: CC1CC2CC1CC2C(=O)Oc1cccc(C(=O)/C=C/c2ccc(F)cc2)c1]

in Example 2 was dissolved in the c-pentanone solvent at a concentration of 2% by weight, and applied on a polyethylene terephthalate substrate (commercial name: SH71, manufactured by SKC Co., Ltd. in Korea) having a thickness of 80 micron by roll coating process, so that the polyethylene terephthalate substrate had a thickness of 1000 Å after drying. Next, the substrate was heated in an oven at 80° C. for 3 min to remove the solvent inside of coating film, and thus a coating film was formed.

The exposing was performed using a high pressure mercury lamp having an intensity of 200 mW/cm² as a light source while polarized UV perpendicular to the proceeding direction of the film was radiated on the coating film using a Wire-grid polarizer manufactured by Moxtek, Co., Ltd. for 5 sec, so that the alignment was provided to form an alignment film.

Next, the solid having 95.0% by weight of UV-polymerizable cyanobiphenyl acrylate and 5.0% by weight of Irgacure 907 (manufactured by Ciba-Geigy, Co., Ltd. in Switzerland) as a photoinitiator was dissolved in toluene to prepare a polymerizable reactive liquid crystal solution, in which the content of the liquid crystal was 25 parts by weight based on 100 parts by weight of the liquid crystal solution.

The prepared liquid crystal solution was applied on the photo-alignment film that was formed by a roll coating process, so that the film had a thickness of 1 μm after drying, and it was dried at 80° C. for 2 min to align the liquid crystal molecules. The non-polarized UV was radiated on the aligned liquid crystal film using a high-pressure mercury lamp having the intensity of 200 mW/cm² as a light source so as to fix the alignment state of the liquid crystals, thereby manufacturing the retardation film.

The alignment properties with respect to the manufactured retardation film were compared with each other by measuring transmittance of the light leakage between the polarizing plates, and the quantitative retardation value was measured using Axoscan (manufactured by Axomatrix, Co., Ltd.).

What is claimed is:

1. A compound having a photoreactive functional group, represented by the following Formula 1:

A-R  [Formula 1]

wherein A is a cyclic olefin-based ring,

R is one or more functional groups substituted in A, in which at least one is a radical of the following Chemical Formula 1a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 1a]

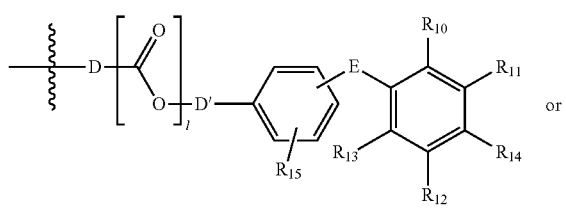

or

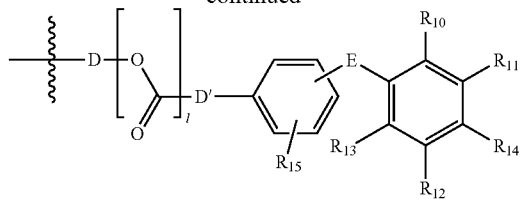

-continued wherein l is 0 or 1,

D and D' are each independently selected from the group consisting of a single bond, nitrogen, oxygen, sulfur, substituted or unsubstituted, linear or branched alkylene having 1 to 20 carbon atoms; substituted or unsubstituted cycloalkylene having 3 to 12 carbon atoms; substituted or unsubstituted, linear or branched alkylene oxide having 1 to 20 carbon atoms; and substituted or unsubstituted cycloalkylene oxide having 3 to 12 carbon atoms, E is

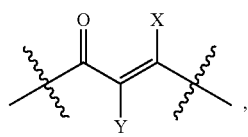

X and Y are each independently selected from the group consisting of hydrogen; halogen; cyano; and substituted or unsubstituted, linear or branched alkyl having 1 to 20 carbon atoms, $R_{10}$, $R_{11}$, $R_{12}$, $R_{13}$, and $R_{14}$ are each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms, R15 is one or two substituent(s), and each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms.

2. The compound according to claim 1, represented by the following Formula 1b:

[Formula 1b]

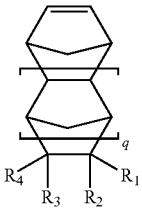

wherein q is an integer of 0 to 4, at least one of $R_1$, $R_2$, $R_3$ and $R_4$ is a radical of Chemical Formula 1a, and the others are each independently selected from the group consisting of hydrogen; halogen; cyano; substituted or unsubstituted, linear or branched alkyl having 1 to 20carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

3. A photoreactive polymer comprising a repeating unit of the following Chemical Formula 1:

[Chemical Formula 1]

wherein m is 50 to 5000,

A' is a cyclic olefin-based repeating unit,

R is one or more functional groups substituted in A', in which at least one is a radical of the following Chemical Formula 1a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 1a]

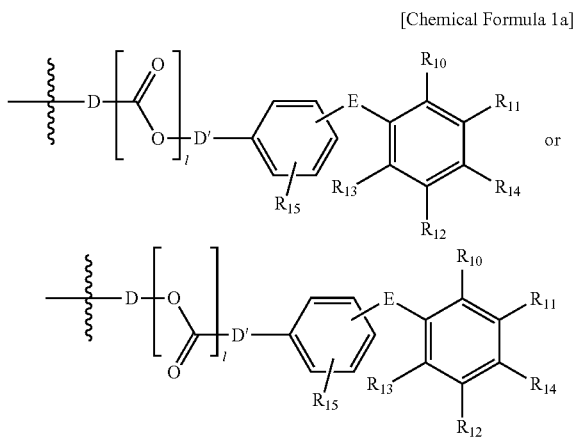

wherein l is 0 or 1,

D and D' are each independently selected from the group consisting of a single bond, nitrogen, oxygen, sulfur, substituted or unsubstituted, linear or branched alkylene having 1 to 20 carbon atoms; substituted or unsubstituted cycloalkylene having 3 to 12 carbon atoms; substituted or unsubstituted, linear or branched alkylene oxide having 1 to 20 carbon atoms; and substituted or unsubstituted cycloalkylene oxide having 3 to 12 carbon atoms, E is

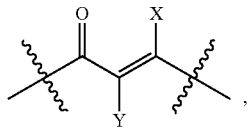,

X and Y are each independently selected from the group consisting of hydrogen; halogen; cyano; and substituted or unsubstituted, linear or branched alkyl having 1 to 20 carbon atoms, $R_{10}, R_{11}, R_{12}, R_{13}$, and $R_{14}$ are each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms, and R15 is one or two substituent(s), and each independently selected from the group consisting of hydrogen, halogen, cyano, substituted or unsubstituted alkyl having 1 to 20 carbon atoms; substituted or unsubstituted alkoxy having 1 to 20 carbon atoms; substituted or unsubstituted aryloxy having 6 to 30 carbon atoms; substituted or unsubstituted aryl having 6 to 40 carbon atoms; hetero aryl having 6 to 40 carbon atoms that includes Group 14, 15 or 16 hetero elements; and substituted or unsubstituted alkoxyaryl having 6 to 40 carbon atoms.

4. The photoreactive polymer according to claim 3, further comprising one or more repeating units selected from the group consisting of the following Chemical Formulae 2 and 3:

[Chemical Formula 2]

[Chemical Formula 3]

wherein n and o are each independently 50 to 5000,

A" is a cyclic olefin-based repeating unit,

B is an olefin-based repeating unit,

R' is one or more functional groups substituted in A", in which at least one is a radical of the following Chemical Formula 2a, and the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms, R" is one or more functional groups substituted in B, and each independently selected from the group consisting of a radical of Chemical Formula 1a; a radical of Chemical Formula 2a; hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms,

[Chemical Formula 2a]

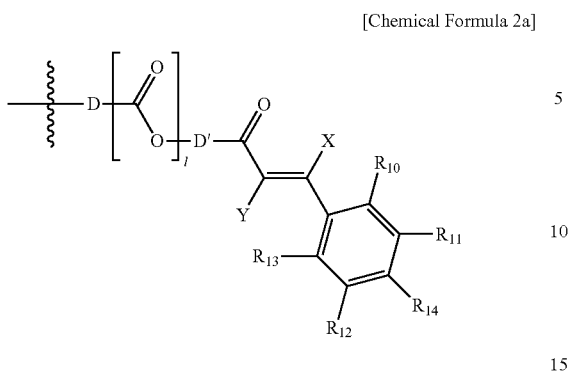

wherein l, D, D', X, Y, $R_{10}$, $R_{11}$, $R_{12}$, $R_{13}$, and $R_{14}$ are the same as defined in Chemical Formula 1a, and are the same as or different from those in Chemical Formula 1a.

5. The photoreactive polymer according to claim 3, wherein at least one of $R_{10}$, $R_{11}$, $R_{12}$, $R_{13}$, and $R_{14}$ is halogen or halogen-substituted alkyl having 1 to 20 carbon atoms.

6. The photoreactive polymer according to claim 5, wherein at least one of $R_{10}$, $R_{11}$, $R_{12}$, $R_{13}$, and $R_{14}$ is fluorine or fluorine-substituted alkyl having 1 to 20 carbon atoms.

7. The photoreactive polymer according to claim 3, wherein the repeating unit of Chemical Formula 1 is a norbornene-based repeating unit represented by the following Chemical Formula 1b or 1c:

[Chemical Formula 1b]

[Chemical Formula 1c]

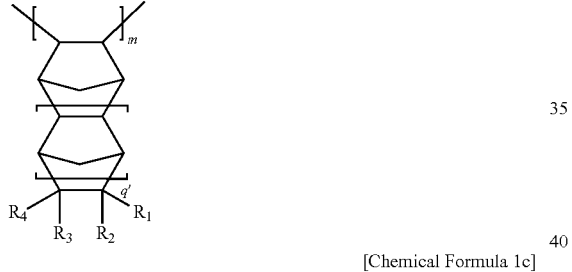

wherein m is 50 to 5000,
q is an integer of 0 to 4,
at least one of $R_1$, $R_2$, $R_3$ and $R_4$ is a radical of Chemical Formula 1a, and
the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

8. The photoreactive polymer according to claim 4, wherein the repeating unit of Chemical Formula 2 is a norbornene-based repeating unit represented by the following Chemical Formula 2b or 2c:

[Chemical Formula 2b]

[Chemical Formula 2c]

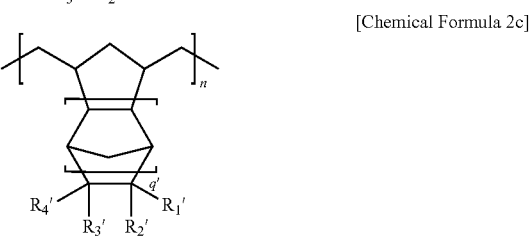

wherein n is 50 to 5000,
q' is an integer of 0 to 4,
at least one of $R_1'$, $R_2'$, $R_3'$ and $R_4'$ is a radical of Chemical Formula 2a, and
the others are each independently selected from the group consisting of hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

9. The photoreactive polymer according to claim 4, wherein the repeating unit of Chemical Formula 3 is an olefin-based repeating unit represented by the following Chemical Formula 3a:

[Chemical Formula 3a]

wherein o is 50 to 5000, and
$R_1''$, $R_2''$, $R_3''$ and $R_4''$ are each independently selected from the group consisting of a radical of Chemical Formula 1a; a radical of Chemical Formula 2a; hydrogen; halogen; cyano; substituted or unsubstituted, linear or branched alkyl having 1 to 20 carbon atoms; substituted or unsubstituted, linear or branched alkenyl having 2 to 20 carbon atoms; substituted or unsubstituted, linear or branched alkynyl having 2 to 20 carbon atoms; substituted or unsubstituted cycloalkyl having 3 to 12 carbon atoms; and substituted or unsubstituted aryl having 6 to 40 carbon atoms.

10. The photoreactive polymer according to claim 4, wherein each of the repeating units of Chemical Formulae 2 and 3 is included at a ratio of 0.1-2.0 mol and 0.1-2.0 mol, based on 1 mol of the repeating unit of Chemical Formula 1.

11. The photoreactive polymer according to claim 7, wherein $R_1$ of the norbornene-based repeating unit is a radical of Chemical Formula 1a.

12. The photoreactive polymer according to claim 8, wherein $R_1'$ of the norbornene-based repeating unit is a radical of Chemical Formula 2a.

13. The photoreactive polymer according to claim 3, wherein the substituted or unsubstituted aryl having 6 to 40 carbon atoms; or the hetero aryl having 6 to 40 carbon atoms that includes Group 14, 15 or 16 hetero elements is selected from the group consisting of the functional groups listed as follows:

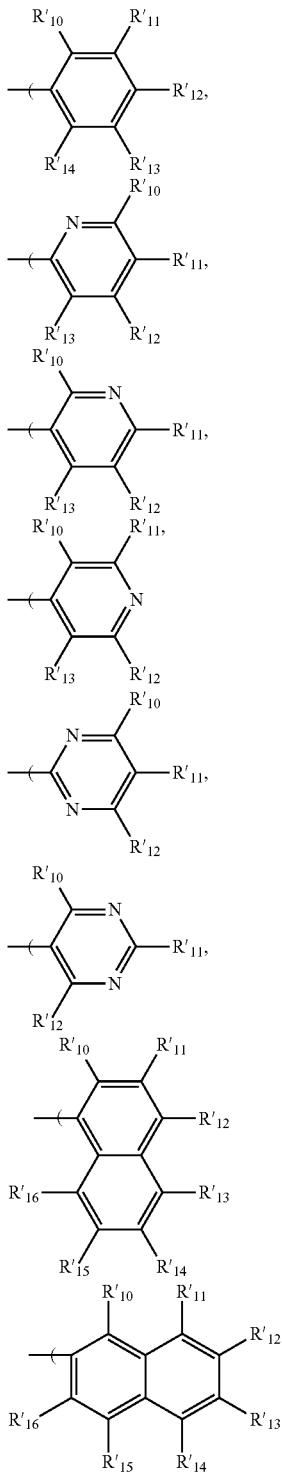

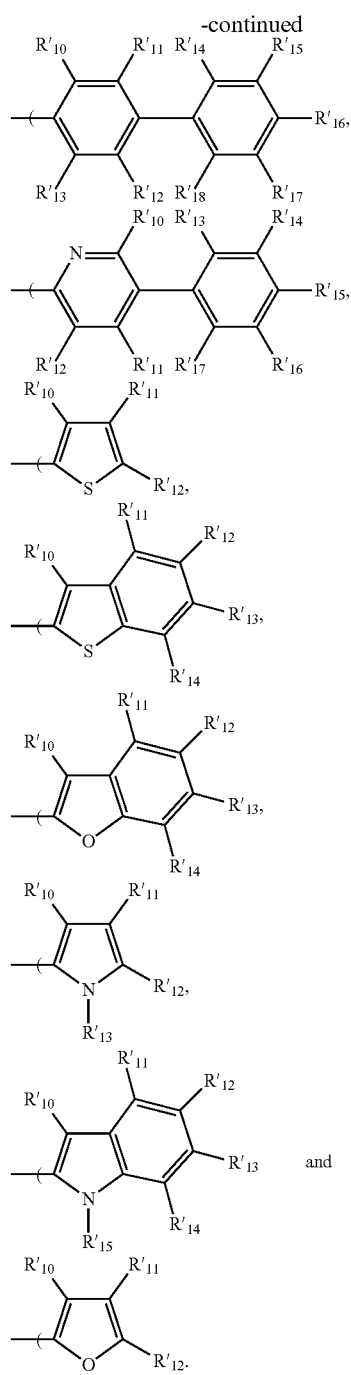

wherein $R'_{10}$ to $R'_{18}$ are each independently selected from the group consisting of substituted or unsubstituted, linear or branched alkyl having 1 to 20 carbon atoms, substituted or unsubstituted alkoxy having 1 to 20 carbon atoms, substituted or unsubstituted aryloxy having 6 to 30 carbon atoms, and substituted or unsubstituted aryl having 6 to 40 carbon atoms.

14. The photoreactive polymer according to claim 3, wherein the photoreactive polymer has a weight-average molecular weight of 10000 to 1000000.

15. An alignment film comprising the photoreactive polymer of claim 3.

* * * * *